United States Patent
Haruna et al.

(10) Patent No.: US 10,581,227 B2
(45) Date of Patent: Mar. 3, 2020

(54) DISCHARGE UNIT

(71) Applicant: DAIKIN INDUSTRIES, LTD., Osaka-shi, Osaka (JP)

(72) Inventors: Shunji Haruna, Osaka (JP); Tatsumi Enokida, Osaka (JP); Kei Suzumura, Osaka (JP); Kiyoshi Kuroi, Osaka (JP); Toshio Tanaka, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 363 days.

(21) Appl. No.: 15/538,605

(22) PCT Filed: Dec. 24, 2015

(86) PCT No.: PCT/JP2015/086118
§ 371 (c)(1),
(2) Date: Jun. 21, 2017

(87) PCT Pub. No.: WO2016/104655
PCT Pub. Date: Jun. 30, 2016

(65) Prior Publication Data
US 2017/0346261 A1    Nov. 30, 2017

(30) Foreign Application Priority Data

Dec. 26, 2014 (JP) ................... 2014-265610

(51) Int. Cl.
*H01T 19/04* (2006.01)
*F24F 7/013* (2006.01)
(Continued)

(52) U.S. Cl.
CPC ............... *H01T 19/04* (2013.01); *A61L 9/22* (2013.01); *F24F 7/013* (2013.01); *H01T 23/00* (2013.01);
(Continued)

(58) Field of Classification Search
CPC ...... F24F 3/166; F24F 2221/54; F24F 23/003; F24F 7/013; H01T 19/04; H01T 23/00; A61L 9/22
(Continued)

(56) References Cited

U.S. PATENT DOCUMENTS 7,408,759 B2 *   8/2008   Gefter ................... H01T 23/00
                                                        361/230
8,095,031 B2 *   1/2012   Deguchi ............ G03G 15/0258
                                                        399/100

FOREIGN PATENT DOCUMENTS

EP     3 185 376 A1    6/2015
JP    2005-100936 A    4/2005
(Continued)

OTHER PUBLICATIONS

International Preliminary Report of corresponding PCT Application No. PCT/JP2015/086118 dated Jul. 6, 2017.
(Continued)

*Primary Examiner* — Zeev V Kitov
(74) *Attorney, Agent, or Firm* — Global IP Counselors, LLP

(57) ABSTRACT

A discharge unit includes a discharge electrode, a counter electrode opposed to the discharge electrode, and an insulation member having a surface. The surface is continuous from the discharge electrode to the counter electrode. A wall portion is provided on one side with respect to a discharge region formed by the discharge electrode. The wall portion is configured to suppress a contaminant from adhering to the surface of the insulation member.

18 Claims, 13 Drawing Sheets

(51) Int. Cl.
*F25D 23/00* (2006.01)
*A61L 9/22* (2006.01)
*H01T 23/00* (2006.01)
*F24F 3/16* (2006.01)

(52) U.S. Cl.
CPC ....... *F24F 3/166* (2013.01); *F24F 2003/1682* (2013.01); *F24F 2221/54* (2013.01); *F25D 23/003* (2013.01)

(58) Field of Classification Search
USPC ........................................................ 361/166
See application file for complete search history.

(56) References Cited

FOREIGN PATENT DOCUMENTS

| | | |
|---|---|---|
| JP | 2009-26492 A | 2/2009 |
| JP | 2011-86533 A | 4/2011 |
| JP | 2013-120651 A | 6/2013 |
| WO | 2012/137410 A1 | 10/2012 |

OTHER PUBLICATIONS

International Search Report of corresponding PCT Application No. PCT/JP2015/086118 dated Mar. 15, 2016.
European Search Report of corresponding EP Application No. 15 87 3223.0 dated Jun. 29, 2018.

\* cited by examiner

DISCHARGE UNIT

CROSS-REFERENCE TO RELATED APPLICATIONS

This U.S. National stage application claims priority under 35 U.S.C. § 119(a) to Japanese Patent Application No. 2014-265610, filed in Japan on Dec. 26, 2014, the entire contents of which are hereby incorporated herein by reference.

TECHNICAL FIELD

The present invention relates to a discharge unit.

BACKGROUND ART

There have been conventionally known discharge units which discharge between a discharge electrode and a counter electrode. A discharge unit is mounted on such a device as an air conditioner, an air cleaner, or the like (e.g. Japanese Unexamined Patent Publication No. 2005-100936). In the discharge unit recited in paragraphs 0095 and 0096 and FIG. 7 of Japanese Unexamined Patent Publication No. 2005-100936, a discharge electrode is fixed to an electrode fixing plate of a sheet metal member, and the sheet metal member is fixed to a counter electrode by using a fixing insulator. Specifically, the sheet metal member and the fixing insulator configure an integral supporting member, and this supporting member supports the discharge electrode and the counter electrode.

When such a device as an air conditioner, an air cleaner, or the like is operated to use a discharge unit, conductive contaminants such as tobacco stains included in room air, ammonium nitrate generated by discharging, and the like adhere to a supporting member. In a structure where a discharge electrode and a counter electrode are supported by an integral supporting member, when more contaminants adhere to the supporting member, insulating properties between the discharge electrode and the counter electrode might be deteriorated. Then, when further more contaminants are adhered to cause the discharge electrode to connect to the counter electrode, the discharge electrode and the counter electrode conduct with each other to prevent discharging.

SUMMARY

An object of the present invention is to suppress deterioration of insulating properties between a discharge electrode and a counter electrode in a discharge unit provided with an insulation member having a surface continuous from the discharge electrode to the counter electrode.

A discharge unit of the present invention includes a discharge electrode, a counter electrode which is opposed to the discharge electrode and an insulation member having a surface which is continuous from the discharge electrode to the counter electrode, in which a wall portion which is configured to suppress a contaminant from adhering to the surface of the insulation member is provided on one side with respect to a discharge region formed by the discharge electrode.

DESCRIPTION OF EMBODIMENTS

Figure 1:
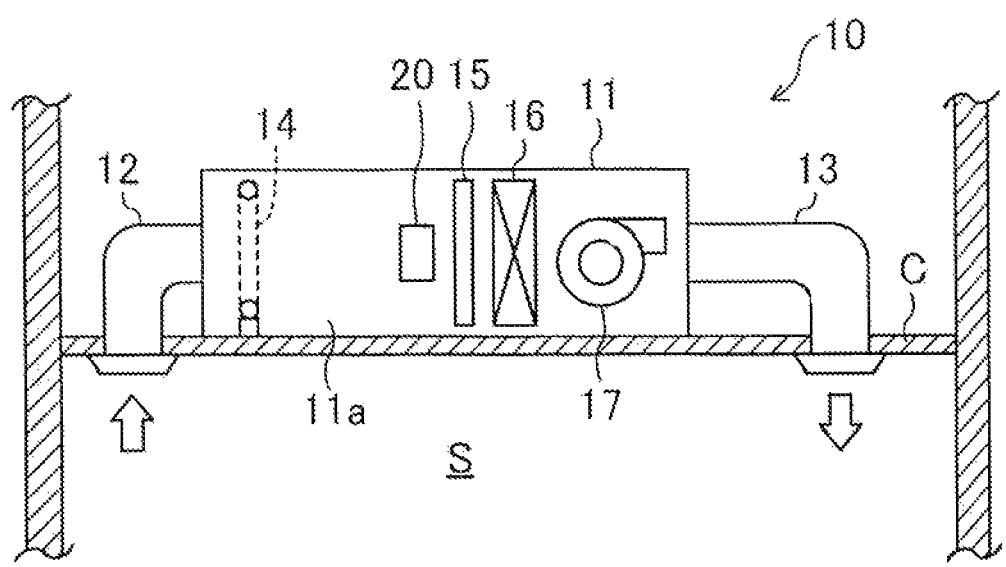
FIG. 1 is a schematic view of a configuration of an air conditioning device including a discharge unit according to an embodiment of the present invention.

In the following, description will be made of a discharge unit according to an embodiment of the present invention with reference to the drawings. As shown in FIG. 1, a discharge unit 20 according to the present embodiment can be mounted in, for example, an air conditioning device 10. The air conditioning device 10 shown in FIG. 1 adjusts temperature of air in a room space S.

[Configuration of Air Conditioning Device]

As shown in FIG. 1, the air conditioning device 10 is disposed on a back face of a ceiling C. The air conditioning device 10 includes an oblong box-shaped air-conditioning casing 11. An inside air duct 12 is connected to one side surface of the air-conditioning casing 11 in a longitudinal direction. An air supply duct 13 is connected to the other side surface of the air-conditioning casing 11 in the longitudinal direction. Inside the air-conditioning casing 11, an air passage 11a is formed. The inside air duct 12 has an inflow end communicating with the room space S and an outflow end communicating with the air passage 11a. The air supply duct 13 has an inflow end communicating with the air passage 11a and an outflow end communicating with the room space S.

In the air passage 11a, a prefilter 14, the discharge unit 20, a catalyst filter 15, a heat exchanger 16, and a fan 17 are arranged sequentially from an upstream side of an air flow (inside air duct 12 side) to a downstream side (air supply duct 13 side). The prefilter 14 collects relatively large dusts in air. The discharge unit 20 generates activated species along with discharging, and the activated species decompose harmful substances and odorous substances in the air.

The catalyst filter 15 is formed, for example, by a honeycomb-structure base material which supports a catalyst on a surface thereof. As the catalyst, manganese-based catalysts, precious metal-based catalysts, or the like are used. The catalyst filter 15 further activates the activated species generated by discharging to promote decomposition of harmful substances and odorous substances in the air. In the catalyst filter 15, an absorbent (e.g., activated carbon) is supported which absorbs harmful substances and odorous substances in the air.

The heat exchanger 16 heats and cools air flowing through the air passage 11*a*. Specifically, the heat exchanger 16 is connected to a refrigerant circuit (not shown). In the refrigerant circuit, a charged refrigerant is circulated to have a refrigeration cycle. The heat exchanger 16 functions as an evaporator which cools air by a low-pressure refrigerant flowing inside thereof. Additionally, the heat exchanger 16 functions as a condenser which heats air by a high-pressure refrigerant flowing inside thereof. The fan 17 carries air in the air passage 11*a*.

[Configuration of Discharge Unit]

Figure 2:
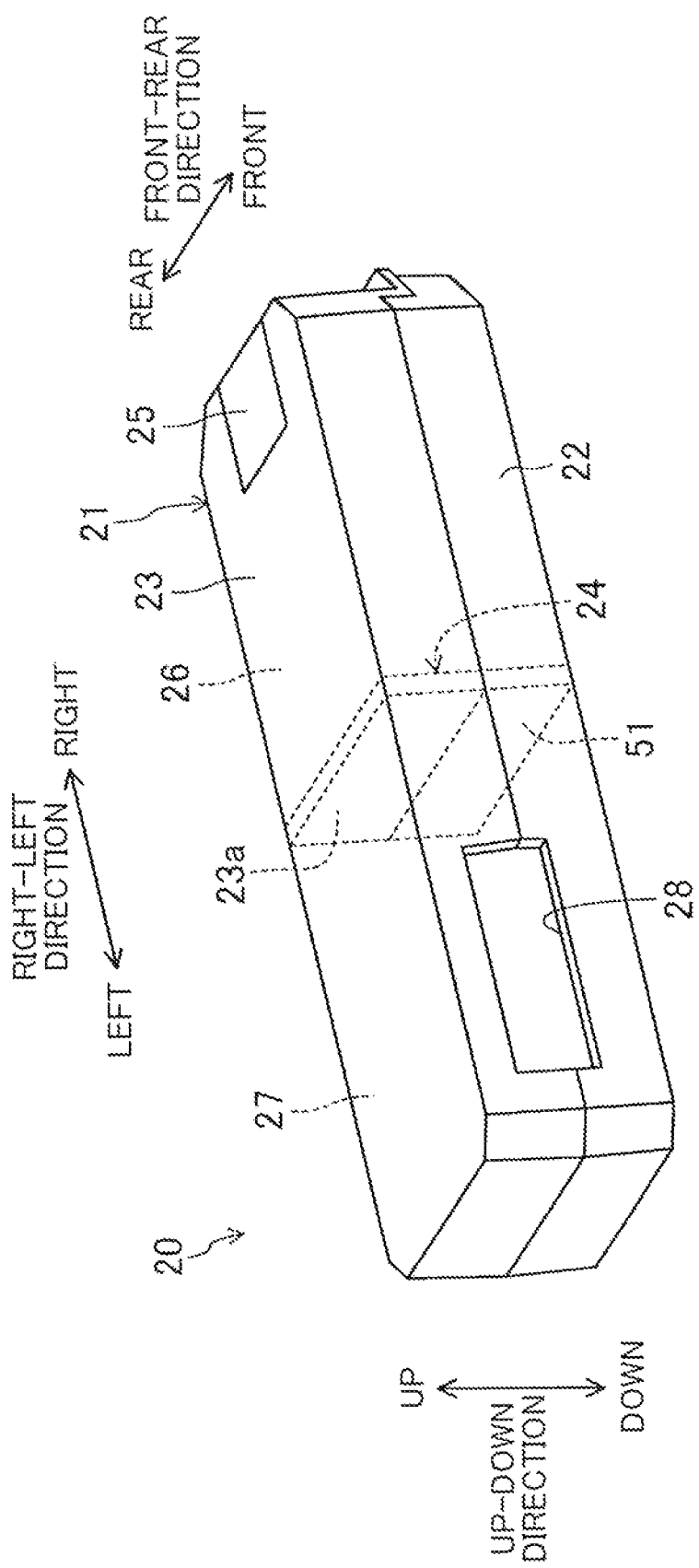
FIG. 2 is a perspective view of a casing of the discharge unit seen from the front side.
Figure 3:
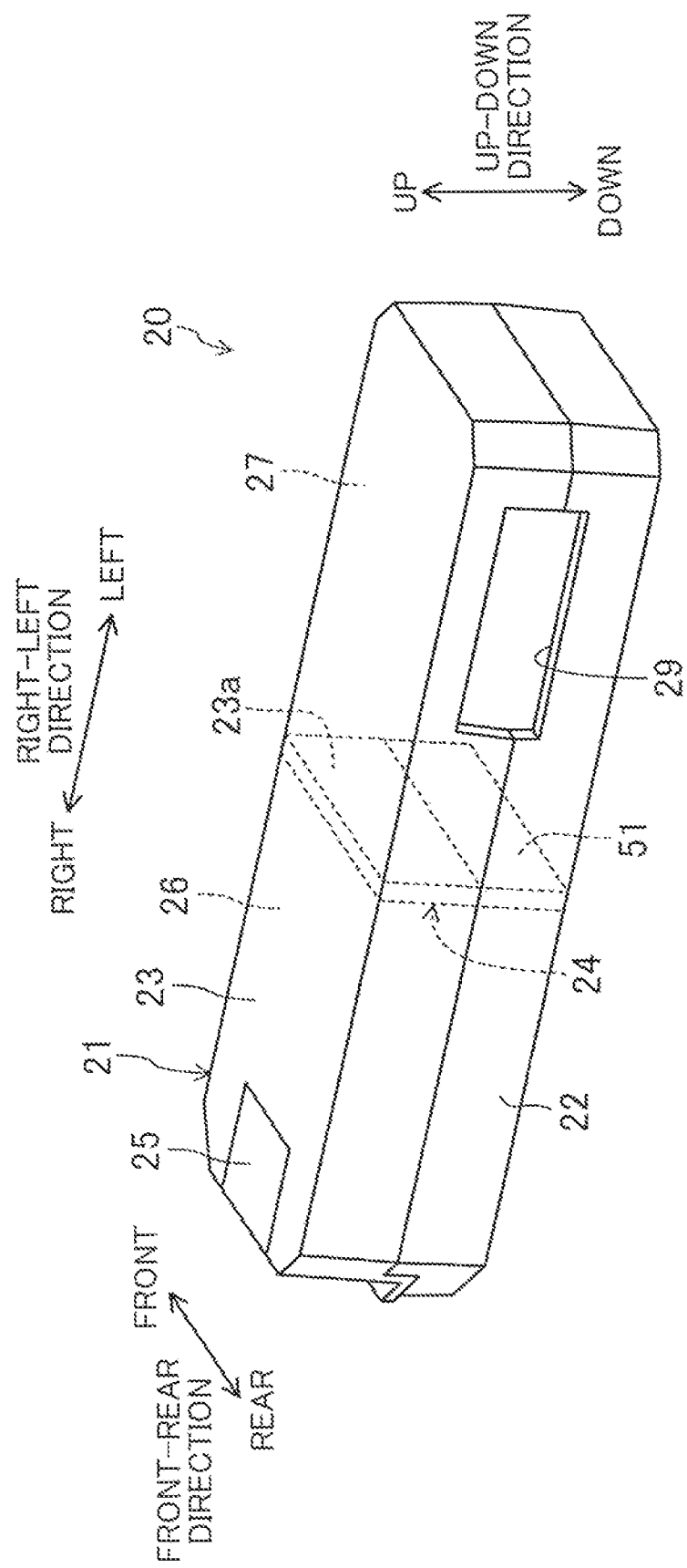
FIG. 3 is a perspective view of the casing of the discharge unit seen from the rear side.
Figure 4:
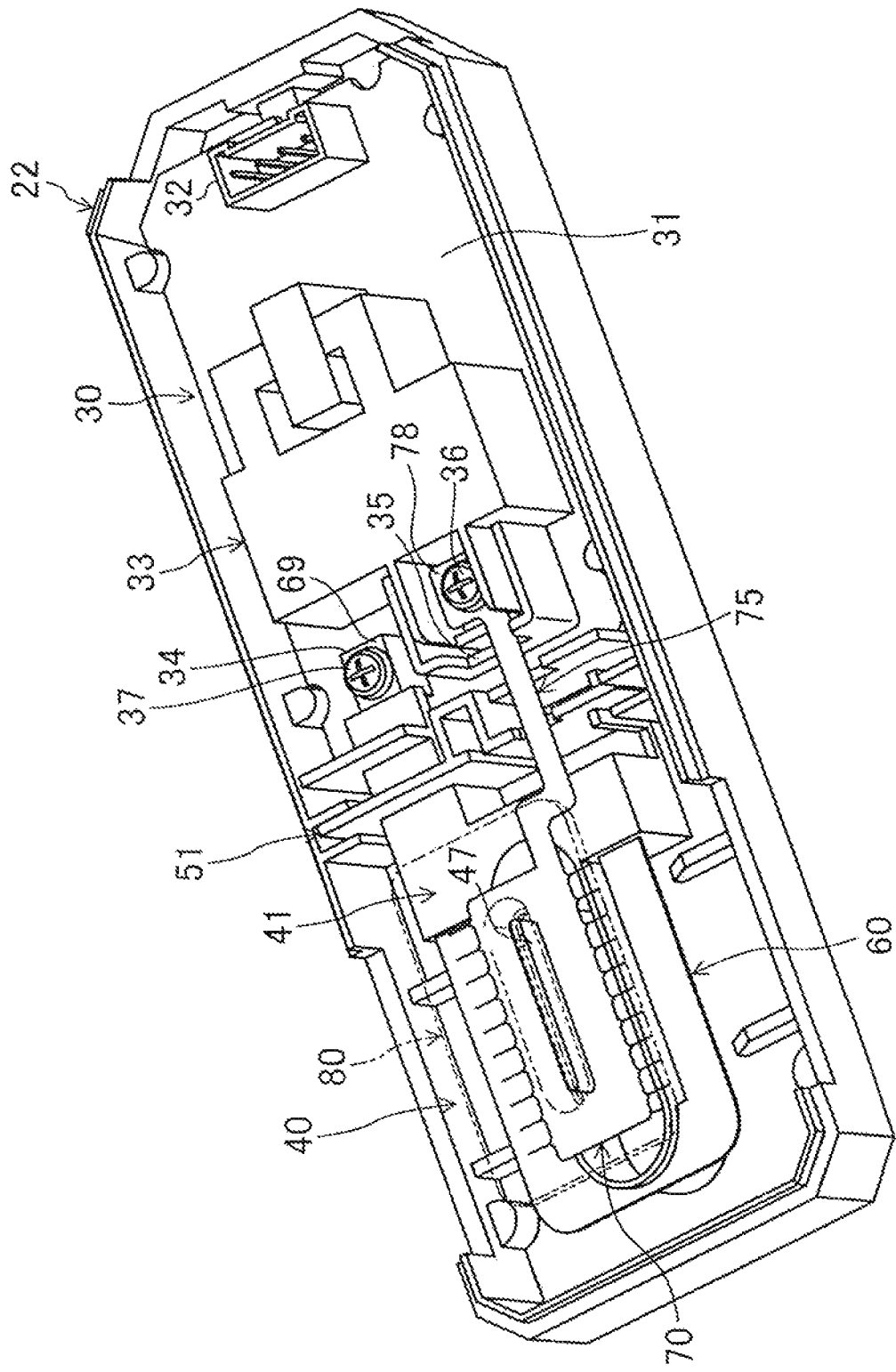
FIG. 4 is a perspective view showing an internal structure of the discharge unit.

The discharge unit 20 is configured to have a streamer discharge system. Specifically, the discharge unit 20 generates low-temperature plasma by streamer discharging, which is followed by generation of highly reactive activated species (high-speed electron, ion, radical, ozone, and the like) in the air. As shown in FIG. 2, FIG. 3, and FIG. 4, the discharge unit 20 includes a casing 21, a voltage supply unit 30 housed in the casing 21, and a discharging processing unit 40 housed in the casing 21.

<Casing>

As shown in FIG. 2 and FIG. 3, the casing 21 is formed in a generally rectangular solid form with an oblong box-shape. The casing 21 is formed of an insulative resin material. The casing 21 is configured with a lower case portion 22, and an upper case portion 23 attached to the top portion of the lower case portion 22. Inside the casing 21, a partition portion 24 is provided at a middle part of the casing 21 in a longitudinal direction (right-left direction) thereof. The partition portion 24 partitions an inner part of the casing 21 into two, right and left spaces. Of these spaces, the right space forms a housing chamber 26 and the left space forms a processing chamber 27 (ventilation passage).

The partition portion 24 is configured with an upper partition wall 23*a* and a lower partition wall 51. The upper partition wall 23*a* is integrally formed inside the upper case portion 23. The lower partition wall 51 is formed integrally with an insulation member 41, which will be detailed later. In the partition portion 24, the upper partition wall 23*a* and the lower partition wall 51 are arranged vertically adjacent to each other such that a lower face of the upper partition wall 23*a* and an upper face of the lower partition wall 51 are in contact with each other.

As shown in FIG. 2, in a front face of the casing 21, a first vent 28 (inflow port) is formed. The first vent 28 is arranged in a part closer to the left side of the casing 21 so as to communicate with the processing chamber 27. Air flown into the first vent 28 flows to the inside of the processing chamber 27.

As shown in FIG. 3, in a rear face of the casing 2.1, a second vent 29 (outflow port) is formed. The second vent 29 is arranged in a part closer to the left side of the casing 21 so as to communicate with the processing chamber 27. The air inside the processing chamber 27 flows out of the casing 21.

As shown in FIG. 2 and FIG. 3, a slide cover 25 is provided at a right end in the middle of the upper case portion 23 in a front-rear direction. The slide cover 25 is formed to be detachable from a main body of the casing 21. When the slide cover 25 is removed, a connector 32 of the voltage supply unit 30 (see FIG. 4) is exposed to the outside of the casing 21.

<Voltage Supply Unit>

As shown in FIG. 4, the voltage supply unit 30 is arranged in the housing chamber 26. The voltage supply unit 30 is configured to supply a power supply voltage supplied from an external power supply to the discharging processing unit 40. The voltage supply unit 30 includes a substrate 31, the connector 32, a power supply transformer 33, and an earth terminal portion 34. The substrate 31 is disposed in the vicinity of a bottom portion of the housing chamber 26. The substrate 31 is formed to be laterally oblong plate-shaped and is arranged over an entire region of the housing chamber 26.

The connector 32 is disposed on an upper face of a right end portion of the substrate 31. The connector 32 is exposed to the outside of the casing 21 by removing the above-described slide cover 25. To the connector 32, a wire to be electrically linked to the external power supply is connected.

The power supply transformer 33 is disposed on the upper face closer to the left side of the substrate 31. The power supply transformer 33 is configured to raise a voltage which is supplied via the connector 32. In a left end portion of the power supply transformer 33, a supply terminal portion 35 is provided. A feeder plate 75 of a discharge electrode 70 is fixed to the supply terminal portion 35 via a fastening member (screw 38).

The earth terminal portion 34 is disposed on the upper face closer to the left side and on the rear side of the substrate 31. An earth plate (not shown) of a counter electrode 60 is fixed to the earth terminal portion 34 via a fastening member (screw 37).

<Discharging Processing Unit>

Figure 5:
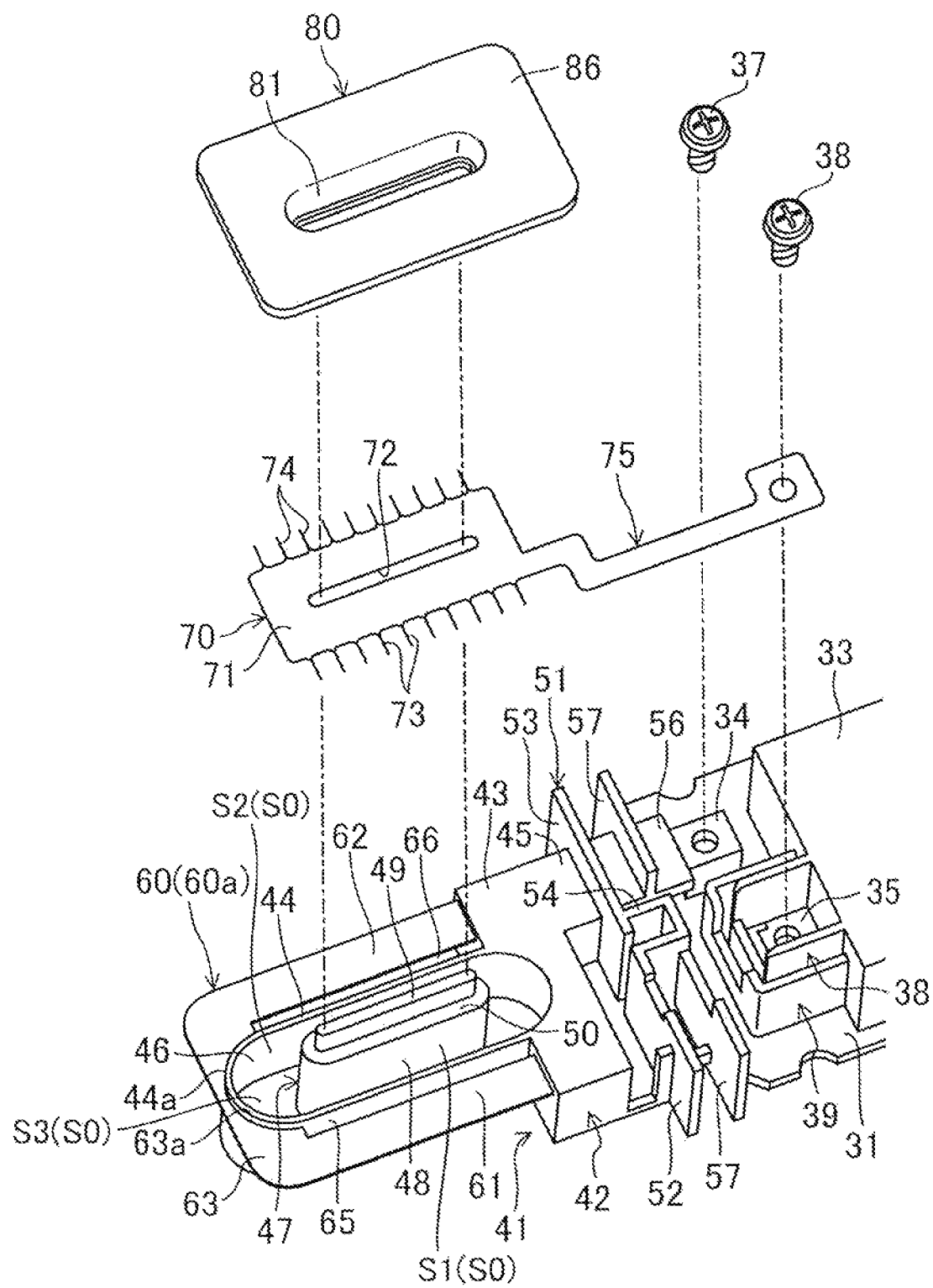
FIG. 5 is an assembly view of a discharging processing unit and a peripheral device thereof in the discharge unit.

As shown in FIG. 4 and FIG. 5, the discharging processing unit 40 is generally arranged in the processing chamber 27. The discharging processing unit 40 is configured to cause streamer discharging to purify air. The discharging processing unit 40 includes the insulation member 41, the counter electrode 60, the discharge electrode 70, and a stabilizer 80.

The insulation member 41 is formed of an insulative resin material and configures a supporting member which supports the discharge electrode 70 and the counter electrode 60 while insulating the same. The counter electrode 60 and the discharge electrode 70 are formed of a conductive metal material. The counter electrode 60 is electrically connected to an earth connection portion 69 to be grounded. The discharge electrode 70 is electrically connected to the voltage supply unit 30 and is supplied with a high voltage (e.g., 7.0 kV). When a voltage is supplied from the voltage supply unit 30 to the discharge electrode 70, a streamer discharge is generated between both electrodes 60 and 70. The stabilizer 80 is formed of a conductive resin material and is at the same potential of the discharge electrode 70. The stabilizer 80 configures a conductive member (fixing member) for forming a stable electric field in the vicinity of the discharge electrode 70.

<Insulation Member>

As shown in FIG. 4, the insulation member 41 is disposed at a bottom of the lower case portion 22. As shown also in FIG. 5, the insulation member 41 includes a joint portion 42, a base portion 44, a supporting portion 47, and the lower partition wall 51.

The joint portion 42 is disposed on the left side of the lower partition wall 51 in the processing chamber 27. The joint portion 42 has a main body portion 43 and a connection portion 45. The main body portion 43 is formed to have a rectangular solid form extending from a front edge to a rear edge of the lower case portion 22. The connection portion 45 is formed continuously between a rear end portion of a right side surface of the main body portion 43 and the lower partition wall 51.

The base portion 44 extends and protrudes from a middle part of a left side surface of the main body portion 43 in the front-rear direction. The base portion 44 has a pair of opposed wall portions standing upward from the bottom of the lower case portion 22 and extending parallel to each other, and a U-shaped joint wall portion linking distal ends of the opposed wall portions. The paired opposed wall portions are spaced apart from each other in the front-rear direction. This forms an arc portion 44a with an arc-shaped cross section in the base portion 44 in the insulation member 41, an oval groove 46 (recessed portion) is formed from the base portion 44 to the middle part of the main body portion 43. The oval groove 46 is a laterally oblong elliptic column-shaped groove with a lower side blocked and an upper side opened.

The supporting portion 47 is arranged in a middle part of the oval groove 46 in the right-left direction and in the front-rear direction. The supporting portion 47 has a supporting portion main body 48 and a protrusion portion 49 (engagement portion) protruding upwardly from the supporting portion main body 48. The supporting portion main body 48 is formed in a pillar shape with a transverse section having a laterally oblong oval shape.

The protrusion portion 49 is disposed in a middle part of the supporting portion main body 48 in the right-left direction and in the front-rear direction. Similarly to the supporting portion main body 48, the protrusion portion 49 is formed in a pillar shape with a transverse section having a laterally oblong oval shape. A height, a width in the right-left direction, and a thickness in the front-rear direction of the protrusion portion 49 are all smaller than those of the supporting portion main body 48. Accordingly, on an upper end surface of the supporting portion main body 48, an oblong and oval annular placement surface 50 is formed around the protrusion portion 49. The placement surface 50 is formed to be a generally horizontal plane. The supporting portion 47 supports the discharge electrode 70 and the stabilizer 80.

The lower partition wall 51 extends from the front edge to the rear edge of the lower case portion 22. The lower partition wall 51 is arranged closer to a front side of the lower case portion 22.

<Counter Electrode>

As shown in FIG. 4 and FIG. 5, the counter electrode 60 is supported by the insulation member 41. The counter electrode 60, which can be molded integrally, for example, with the insulation member 41, is not limited thereto, but may be formed separately. In integral molding, the counter electrode 60 and the insulation member 41 are configured to be an integral unit by insert molding. The counter electrode 60 is formed to have such a flat plate-shape as to be located on the same plane (horizontal plane) as a whole. The counter electrode 60 includes a rectangular frame-shaped counter electrode main body 60a, and an earth plate (not shown) which extends rightward from a rear portion on the right side of the counter electrode main body 60a and is fixed to the earth terminal portion 34.

The counter electrode main body 60a is configured with a first opposed plate 61, a second opposed plate 62, a first joint plate 63, and a second joint plate (not shown) which are annularly combined. The first opposed plate 61 is located on a front side of the counter electrode main body 60a and extends in the right-left direction. The second opposed plate 62 is located on a rear side of the counter electrode main body 60a and extends in the right-left direction. Between the first opposed plate 61 and a front face of the base portion 44, an oblong rectangular front side space portion 65 is formed. Between the second opposed plate 62 and a rear face of the base portion 44, an oblong rectangular rear side space portion 66 is formed.

The first joint plate 63 is located on the left side of the counter electrode main body 60a to extend in the front-rear direction. The first joint plate 63 joins a left end of the first opposed plate 61 and a left end of the second opposed plate 62. On an inner edge (right side) of the first joint plate 63, an arc groove 63a with which the arc portion 44a of the base portion 44 engages is formed. The second joint plate is located on the right side of the counter electrode main body 60a to extend in the front-rear direction. The second joint plate joins a right end of the first opposed plate 61 and a right end of the second opposed plate 62. The second joint plate is embedded in a top portion of the main body portion 43.

<Discharge Electrode>

As shown in FIG. 4 and FIG. 5, the discharge electrode 70 is supported on a top portion of the insulation member 41. The discharge electrode 70 is formed to be such a thin plate as to be located on the same plane (on the horizontal plane) as a whole. A thickness of the discharge electrode 70 is extremely small as compared with a thickness of the counter electrode 60. The discharge electrode 70 includes an electrode supporting plate 71, a plurality of discharging needles 73 and 74 supported in a side edge portion of the electrode supporting plate 71, and a feeder plate 75 extending and protruding rightward from a front end portion of a right side of the electrode supporting plate 71. The feeder plate 75 is connected to the supply terminal portion 35 via the screw 38.

The electrode supporting plate 71 is arranged above the base portion 44. The electrode supporting plate 71 extends in the right-left direction along the base portion 44. At a center of the electrode supporting plate 71 (in a middle part of the electrode supporting plate 71 in a longitudinal direction and a width direction), a positioning hole 72 (opening hole), in which the protrusion portion 49 of the supporting portion 47 fits, is formed. The positioning hole 72 is formed to have a laterally oblong oval shape so as to correspond to a contour of the protrusion portion 49. When the protrusion portion 49 fits in the positioning hole 72, the electrode supporting plate 71 is disposed on the placement surface 50. This maintains flatness of the electrode supporting plate 71. In other words, the electrode supporting plate 71 is supported in a horizontal state by the placement surface 50.

At a front edge of the electrode supporting plate 71, the plurality of long needle-shaped or bar-shaped first discharging needles 73 are supported. The plurality of first discharging needles 73 are aligned at intervals along the front edge of the electrode supporting plate 71 to straightly and horizontally extend forward from the electrode supporting plate 71. The first discharging needles 73 are arranged in parallel to each other. At a rear edge of the electrode supporting plate 71, the plurality of long needle-shaped or bar-shaped second discharging needles 74 are supported. The plurality of second discharging needles 74 are aligned at intervals along the rear edge of the electrode supporting plate 71 to straightly and horizontally extend backward from the electrode supporting plate 71. The second discharging needles 74 are arranged in parallel to each other. The electrode supporting plate 71 is formed to have an oblong shape extending in an alignment direction of the plurality of discharging needles 73 and 74. This enables provision of numerous discharging needles 73 and 74 in the front and rear side edge portions of the electrode supporting plate 71. The plurality of first discharging needles 73 and the plurality of second discharging needles 74 are generally coaxial in the front-rear direction, but may be arranged to be displaced in the right-left direction.

The first discharging needles 73 are parallel to the first opposed plate 61, and the second discharging needles 74 are parallel to the second opposed plate 62. A lower part of a tip of the first discharging needle 73 is opposed to the first opposed plate 61, and a lower part of a tip of the second discharging needle 74 is opposed to the second opposed plate 62.

<Stabilizer>

The stabilizer 80 is arranged above the supporting portion 47 and the discharge electrode 70. The stabilizer 80 includes a tubular wall portion 81 having a tubular shape, and a canopy portion 86 stretching out right and left and backward and forward from an upper end portion of the tubular wall portion 81. In the tubular wall portion 81, the protrusion portion 49 of the insulation member 41 fits. Accordingly, the stabilizer 80 is disposed on the top of the electrode supporting plate 71 to determine a relative positional relation between the stabilizer 80, and the electrode supporting plate 71 and the counter electrode 60.

A contour of the canopy portion 86 is formed to be a laterally oblong rectangular plate. With the protrusion portion 49 being fit in the tubular wall portion 81, the canopy portion 86 is in a generally horizontal state. A front edge of the canopy portion 86 stretches out further frontward than the tips of the first discharging needles 73. A rear edge of the canopy portion 86 stretches out further rearward than the tips of the second discharging needles 74. In other words, a lower face of the canopy portion 86 forms a horizontal plane to be in parallel to the respective discharging needles 73 and 74 so as to follow the respective discharging needles 73 and 74.

[Operation]

The air conditioning device 10 switches between a cooling operation and a heating operation. When the fan 17 of the air conditioning device 10 is operated, air in the room space S is sucked into the air passage 11a via the inside air duct 12. This air passes through the prefilter 14. The prefilter 14 collects relatively large dusts in the air.

The air having passed through the prefilter 14 passes through the discharge unit 20 (see FIG. 2). Specifically, this air flows into the processing chamber 27 from the first vent 28 of the casing 21. In the discharge unit 20, a high voltage is supplied from the power supply transformer 33 of the voltage supply unit 30 to the discharge electrode 70. As a result, streamer discharging progresses from the tip of each of the discharging needles 73 and 74 of the discharge electrode 70 toward the opposed plates 61 and 62 (see FIG. 6). The high voltage is supplied also to the stabilizer 80 to be connected to the discharge electrode 70. This stabilizes the streamer discharging directed from the discharging needles 73 and 74 to the opposed plates 61 and 62.

When the discharging processing unit 40 generates a streamer discharge, activated species are resultantly generated in the air. As a result, harmful substances and odorous substances in the air are oxidized and decomposed by the activated species to purify the air. The air in the processing chamber 27 flows out of the casing 21 from the second vent 29 together with the activated species (see FIG. 3) to pass through the catalyst filter 15. The catalyst adsorbs odorous substances and the like in the air. Decomposition of the adsorbed odorous substances by the activated species leads to reproduction of an adsorbent.

Thus purified air is heated or cooled by the heat exchanger 16, and then supplied to the room space S via the air supply duct 13. This leads to heating or cooling of the room space S, as well as to purification of room air.

[Structure for Suppressing Adhesion of Contaminants]

Next, description will be made of a structure for suppressing adhesion of contaminants in the discharge unit 20 of the present embodiment.

As described above, in the discharge unit 20 of the present embodiment, the discharge electrode 70 and the counter electrode 60 are supported by one member (integral member), i.e., the insulation member 41. In a structure in which the discharge electrode 70 and the counter electrode 60 are thus supported by the insulation member 41 as an integral supporting member, a continuous surface is formed from the discharge electrode 70 to the counter electrode 60.

Specifically, for example, in FIG. 5, the discharge electrode 70 disposed on the placement surface 50 of the supporting portion main body 48 (discharge electrode supporting portion 48) of the insulation member 41 and the counter electrode 60 supported on the base portion 44 (counter electrode supporting portion 44) are continuous by surfaces S1, S2, and S3 in a following manner. Specifically, the discharge electrode 70 and the counter electrode 60 are continuous by a surface S0 of the insulation member 41 including an outer surface S1 of the supporting portion main body 48, an inner surface S2 of the base portion 44, and a bottom surface S3 which links the outer surface S1 and the inner surface S2 at the bottom.

Figure 7:
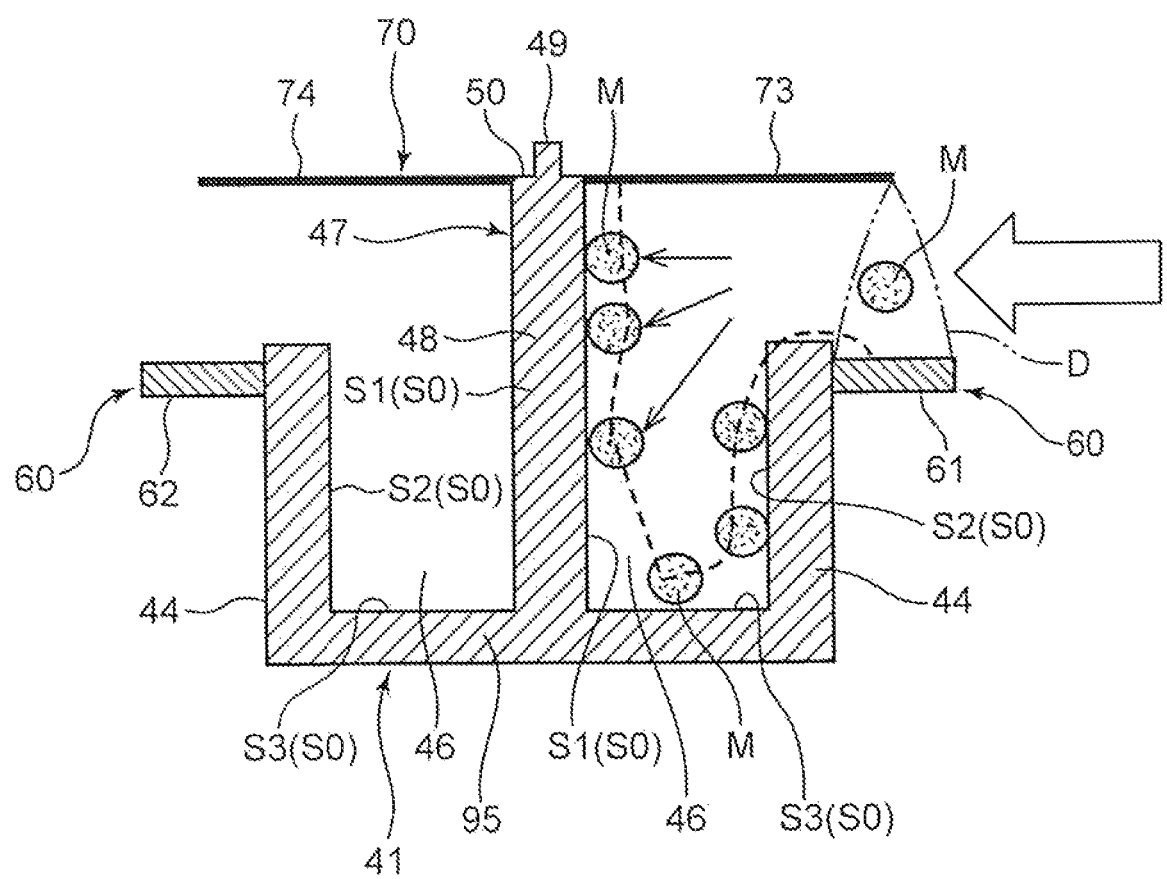
FIG. 7 is a sectional view schematically showing a discharging processing unit in a reference example.

Accordingly, for example, in a discharging processing unit in a discharge unit of a reference example shown in FIG. 7, when adhesion of contaminants to the surface S0 (S1, S2, and S3) of the insulation member 41 progresses, insulating properties between the discharge electrode 70 and the counter electrode 60 might be deteriorated.

Under these circumstances, the discharge unit 20 of the present embodiment is provided with an adhesion suppress structure for suppressing contaminants from adhering to the surface S0 of the insulation member 41.

Figure 8:
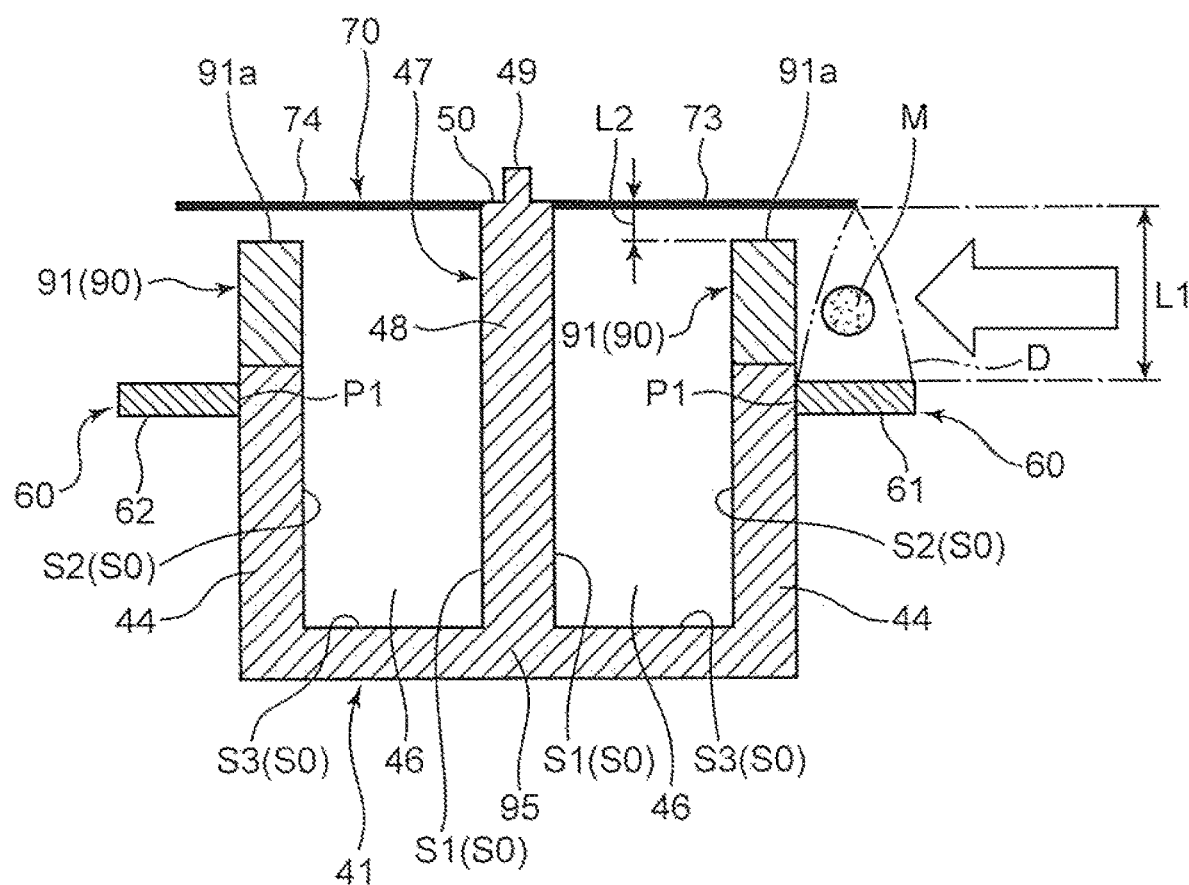
FIG. 8 is a sectional view schematically showing the discharging processing unit in the embodiment, which shows a structure for suppressing adhesion of contaminants in a first structure example.
Figure 10:
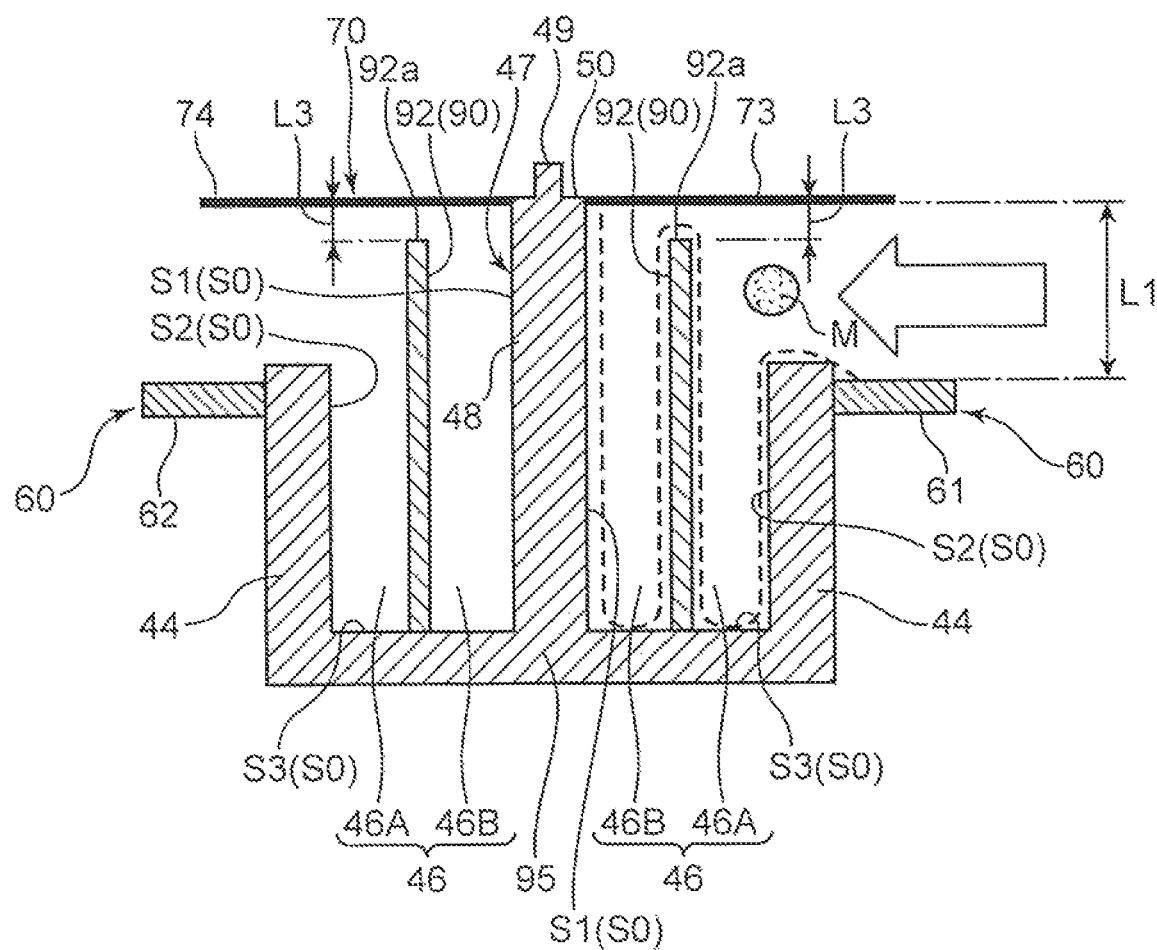
FIG. 10 is a sectional view schematically showing the discharging processing unit in the embodiment, the view showing a structure for suppressing adhesion of contaminants in a second structure example.
Figure 11:
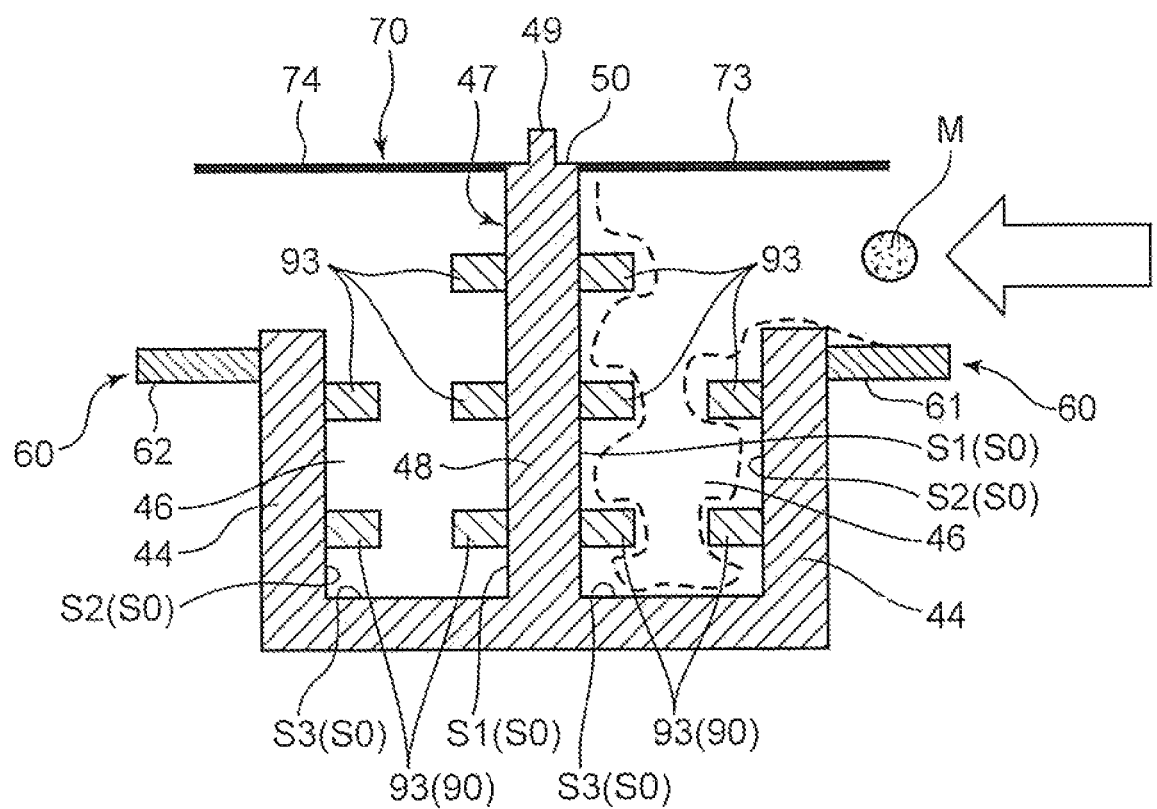
FIG. 11 is a sectional view schematically showing the discharging processing unit in the embodiment, the view showing a structure for suppressing adhesion of contaminants in a third structure example.
Figure 12:
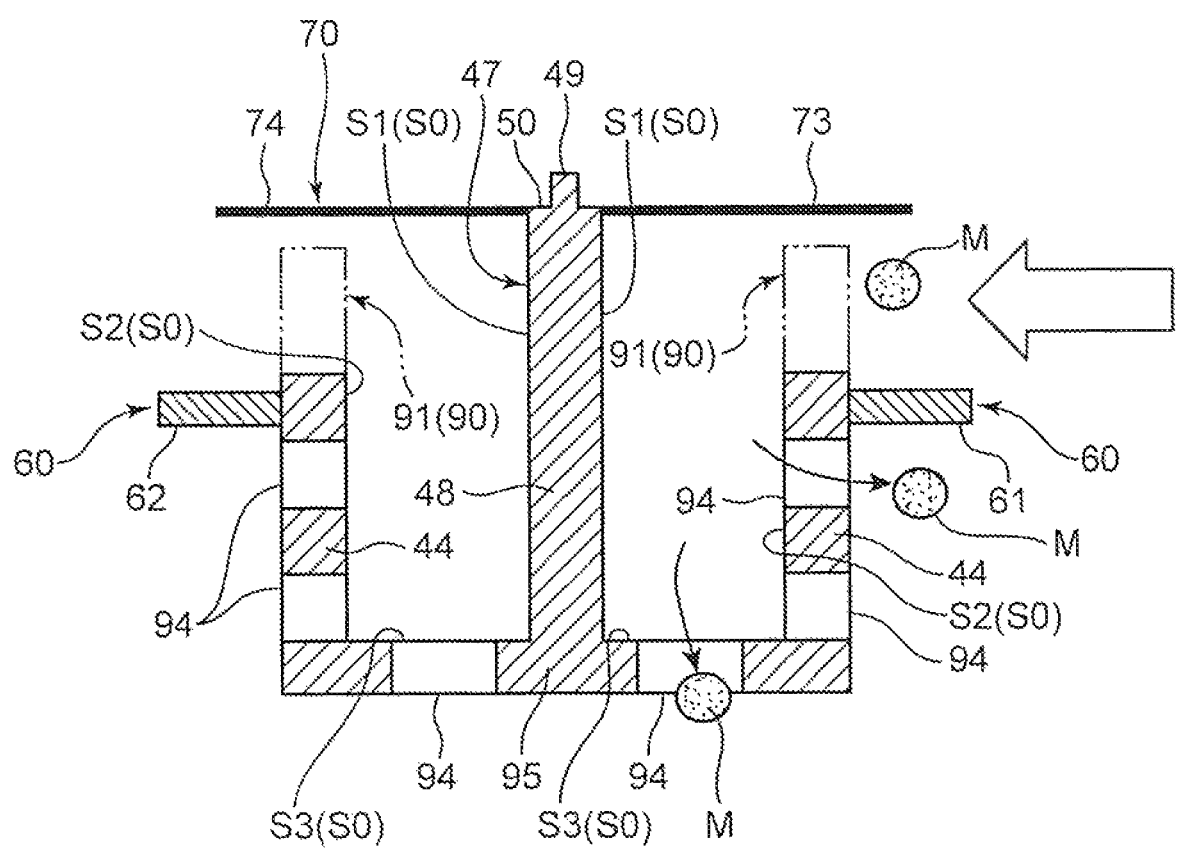
FIG. 12 is a sectional view schematically showing the discharging processing unit in the embodiment, the view showing a structure for suppressing adhesion of contaminants in a fourth structure example.

FIG. 8, and FIG. 10 to FIG. 12 are sectional views showing the discharging processing unit 40 in the present embodiment. FIG. 8 shows a structure for suppressing adhesion of contaminants in a first structure example, FIG. 10 shows a structure for suppressing adhesion of contaminants in a second structure example, FIG. 11 shows a structure for suppressing adhesion of contaminants in a third structure example, and FIG. 12 shows a structure for suppressing adhesion of contaminants in a fourth structure example. Positions of these cross sections are positions taken along line A-A in FIG. 6.

In the adhesion suppress structures shown in the first to fourth structure examples shown in FIG. 8, and FIG. 10 to FIG. 12, a wall portion 90 is provided which suppresses adhesion of contaminants M to the surface of the insulation member 41. The wall portion 90 is provided on one side (inside) with respect to a discharge region D formed by the discharge electrode 70. In the present embodiment, the wall portion 90 is provided closer to the side of the supporting portion main body 48 (the side of the discharge electrode supporting portion 48) than the discharge region D.

In the present embodiment, the wall portion 90 is formed of an insulative material. The wall portion 90 may have a structure fixed to the insulation member 41 after being molded separately from the insulation member 41, or may be integrally molded with the insulation member 41. Additionally, the wall portion 90 may be formed of the same material as that of the insulation member 41 or formed of a material different from that of the insulation member 41.

In the discharge unit 20 of the present embodiment, provision of the wall portion 90 as described above suppresses conductive contaminants M such as ammonium nitrate generated in the discharge region D and tobacco stains contained in room air from adhering to the surface S0 of the insulation member 41. This suppresses deterioration in insulating properties between the discharge electrode 70 and the counter electrode 60 in the insulation member 41 having the surface S0 continuous from the discharge electrode 70 to the counter electrode 60.

Although in the following, the first to fourth structure examples will be specifically described, the structure for suppressing adhesion of contaminants in the discharge unit 20 of the present embodiment is not limited to the following structure.

<First Structure Example>

In FIG. 8, the surface S0 of the insulation member 41 includes the outer surface S1 of the supporting portion main body 48 (discharge electrode supporting portion 48), the inner surface S2 of the base portion 44 (counter electrode supporting portion 44), and the bottom surface S3 which links the outer surface S1 and the inner surface S2 at the bottom of the supporting portion 47. Then, the discharge electrode 70 and the counter electrode 60 are made continuous by the surface S0 (S1, S2, and S3) of the insulation member 41.

Figure 6:
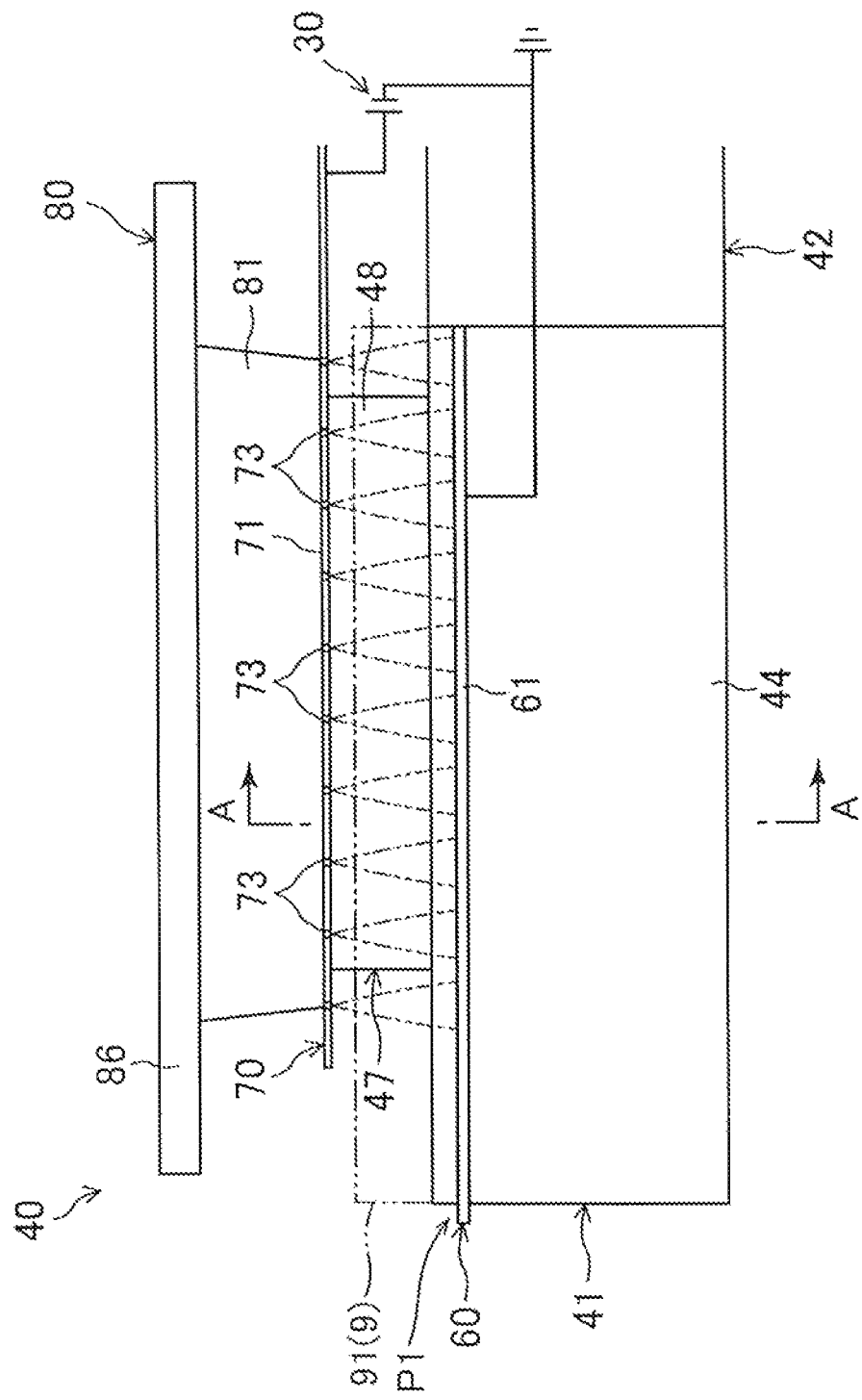
FIG. 6 is a front view of the discharging processing unit.

In the first structure example shown in FIG. 8, the wall portion 90 includes an extension portion 91 extending from an attachment portion P1 of the insulation member 41 to which the counter electrode 60 is attached to the side of the discharge electrode 70. In the present embodiment, the attachment portion P1 is an upper end portion of the base portion 44 (counter electrode supporting portion 44) or a part in the vicinity thereof as shown in FIG. 6 and FIG. 8. The extension portion 91 is arranged in parallel to the counter electrode supporting portion 44 over the entire region where the plurality of discharging needles 73 (74) are provided. A gap is formed between a distal end portion (upper end portion) 91a of the extension portion 91 and the discharging needles 73 and 74.

In the first structure example, the extension portion 91, which extends from the attachment portion P1 to the side of the discharge electrode 70, effectively functions as a barrier which suppresses the contaminants M generated in the discharge region D between the discharge electrode 70 and the counter electrode 60 from entering the surface S0 side of the insulation member 41.

Additionally, provision of the extension portion 91 makes a distance L2 between the discharging needle 73 (74) of the discharge electrode 70 and the extension portion 91 of the wall portion 90 be shorter than a distance L1 between the discharging needle 73 (74) of the discharge electrode 70 and the opposed plate 61 (62) of the counter electrode 60. As a result, the contaminants M such as ammonium nitrate generated in the discharge region D between the discharging needle 73 (74) of the discharge electrode 70 and the opposed plate 61 (62) of the counter electrode 60 and tobacco stains contained in room air are unlikely to pass through the gap between the discharge electrode 70 and the extension portion 91 of the wall portion 90. This enhances an effect of suppressing adhesion of the contaminants M to the surface S0 of the insulation member 41.

Additionally, the distance L2 between the discharging needle 73 (74) of the discharge electrode 70 and the extension portion 91 (upper end portion 91a) of the wall portion 90 is 30% or more and 68% or less of the distance L1 between the discharging needle 73 (74) of the discharge electrode 70 and the opposed plate 61 (62) of the counter electrode 60. In other words, a ratio of the distance L2 to the distance L1 (L2/L1×100%) is 30% or more and 68% or less.

When the distance L2 is less than 30% of the distance L1, provision of the discharging needle 73 (74) and the extension portion 91 close to each other causes discharging to be generated easily. This makes it difficult to exhibit streamer discharging which is to be originally generated between the discharge electrode (70) and the counter electrode (60). By contrast, when the distance L2 exceeds 68% of the distance L1, the contaminants M easily pass through the gap between the discharging needle 73 (74) and the extension portion 91, so that it is difficult to effectively suppress adhesion of the contaminants M to the surfaces S1, S2, and S3 of the insulation member 41. Therefore, the distance L2 is preferably 30% or more and 68% or less of the distance L1, more preferably 40% or more and 60% or less, and most preferably 50%.

Figure 9:
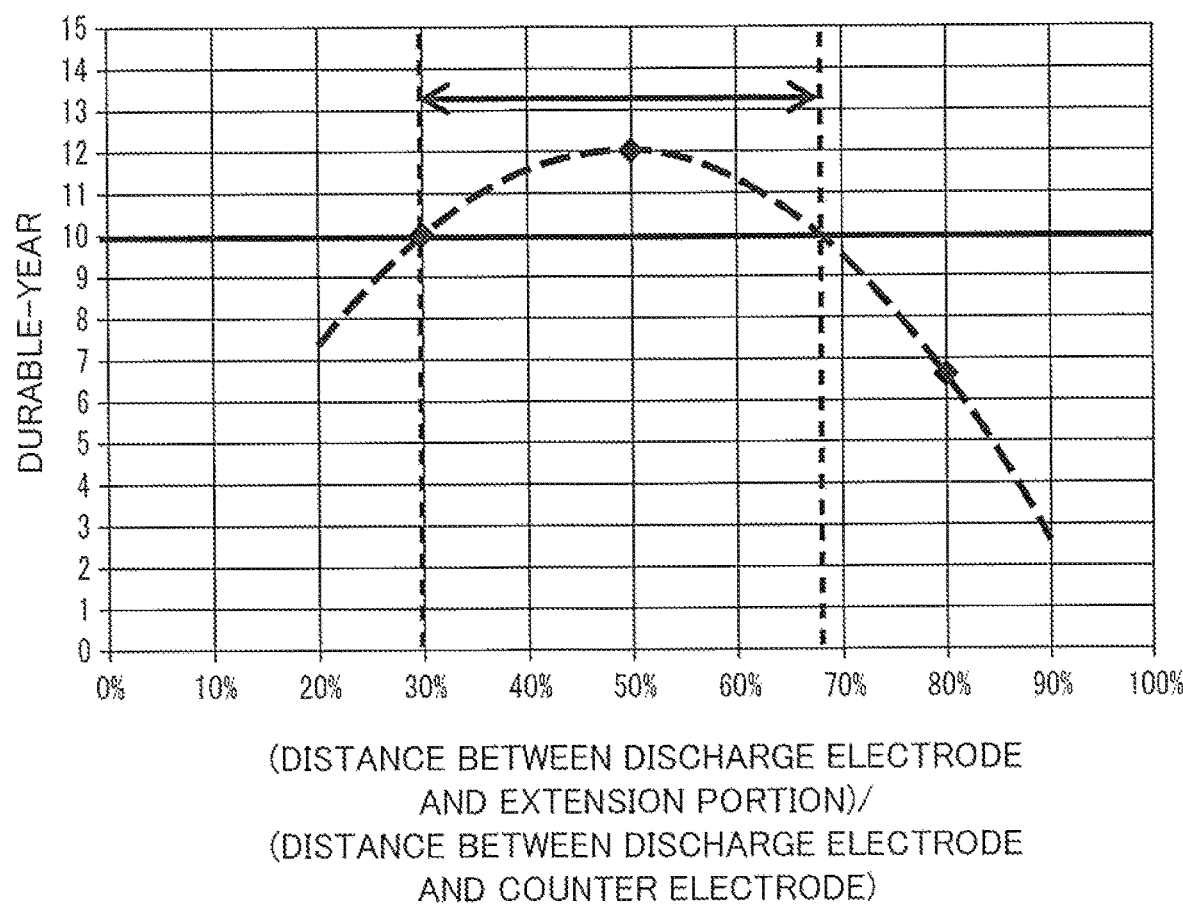
FIG. 9 is a graph showing a relation between a ratio of a distance between a discharge electrode and a wall portion to a distance between the discharge electrode and a counter electrode and a durable-year of the discharge unit.

The graph of FIG. 9 shows an approximate curve of a relation between a ratio of the distance L2 to the distance L1 (the horizontal axis) and a durable-year of the discharge unit 20 (the vertical axis). As is clear from the graph, when the ratio of the distance L2 to the distance L1 is less than 30% and when the same exceeds 68%, a target durable-year (available period) of 10 years cannot be achieved. This is because of discharging generated between the discharging needle 73 (74) and the extension portion 91 or adhesion of contaminants to the surface of the insulation member 41 as described above, and maintenance is required before reaching 10 years of use. By contrast, by setting the ratio of the distance L2 to the distance L1 to be 30% or more and 68% or less, more than 10 years of durable-year can be achieved to enable continuous use of the discharge unit 20 for 10 years without maintenance. In particular, when the ratio of the distance L2 to the distance L1 is 40% or more and 60% or less, the durable-year exceeds 11 years, and when the ratio is 50%, the durable-year reaches the maximum of 12 years.

Additionally, both of the distance between the discharging needle 73 and the extension portion 91 and the distance between the discharging needle 74 and the extension portion 91 may be 30% or more and 68% or less of the distance L1, but the present invention is not limited thereto. In other words, only the distance between the discharging needle 73 located on one side when viewed from the discharge electrode supporting portion 48 and the extension portion 91 may be within the above range, or only the distance between the discharging needle 74 located on the other side when viewed from the discharge electrode supporting portion 48 and the extension portion 91 may be within the above range.

Further, in the first structure example, the distal end portion (upper end portion) 91a of the extension portion 91 is located closer to the discharging needle 73 (74) of the discharge electrode 70 than to the opposed plate 61 (62) of the counter electrode 60. Such location of the distal end portion (upper end portion) 91a of the extension portion 91 further enhances the effect of suppressing adhesion of the contaminants M to the surface S0 of the insulation member 41 as compared with location closer to the opposed plate 61

(62) of the counter electrode 60 than to the discharging needle 73 (74) of the discharge electrode 70.

Additionally, in the present embodiment, since the insulation member 41 has the continuous recessed surface S0 formed by the above surfaces S1, S2, and S3, the surface area of the insulation member 41 is increased to enable a further increase in time until adhesion of the contaminants M to the surface S0 of the insulation member 41 causes conduction between the discharge electrode 70 and the counter electrode 60.

The first structure example can be also used in combination with at least one of second to fourth structure examples to be described later.

<Second Structure Example>

In the second structure example shown in FIG. 10, the wall portion 90 includes a sectioning portion 92 which sections a recessed inner space (i.e., the recessed inner space formed by the recessed portion 46 (oval groove 46)) formed with the discharge electrode supporting portion 48 and the counter electrode supporting portion 44 into a first space 46A and a second space 46B. The first space 46A is located on a side of the discharge region D, and the second space 46B is located on the side opposite to the discharge region D with respect to the first space 46A (in the present embodiment, located on the side of the discharge electrode supporting portion 48), The sectioning portion 92 is a barrier standing from the bottom surface S3 of the supporting portion 47 of the insulation member 41 toward the discharging needle 73 (74) of the discharge electrode 70. The sectioning portion 92 is arranged approximately in parallel to the discharge electrode supporting portion 48 over the entire region where the plurality of discharging needles 73 (74) are provided. A gap is formed between the sectioning portion 92 and the discharge electrode supporting portion 48, and a gap is formed also between the sectioning portion 92 and the counter electrode supporting portion 44. These gaps have substantially the same size. A gap is formed also between the distal end portion (upper end portion) 92a of the sectioning portion 92 and the discharging needles 73 and 74.

In the second structure example, provision of the sectioning portion 92 enables an increase in a creepage distance from the discharge electrode 70 to the counter electrode 60 as indicated by a broken line in FIG. 10.

Additionally, in the second structure example, since the sectioning portion 92 functions as a barrier, the contaminants M are more unlikely to reach the second space 46B as compared with the first space 46A. Therefore, it is possible to effectively suppress adhesion of the contaminants M to the surface forming the second space 46B (the surface S1 and a part of the surface S3) of the surface S0 of the insulation member 41.

From the foregoing, in the second structure example, deterioration in the insulating properties between the discharge electrode 70 and the counter electrode 60 can be suppressed.

Additionally, provision of the sectioning portion 92 makes a distance L3 between the discharging needle 73 (74) of the discharge electrode 70 and the sectioning portion 92 of the wall portion 90 be shorter than the distance L1 between the discharging needle 73 (74) of the discharge electrode 70 and the opposed plate 61 (62) of the counter electrode 60. As a result, the contaminants M such as ammonium nitrate generated in the discharge region D between the discharging needle 73 (74) of the discharge electrode 70 and the opposed plate 61 (62) of the counter electrode 60 and tobacco stains contained in room air are unlikely to pass through the gap between the discharge electrode 70 and the sectioning portion 92 of the wall portion 90. This enhances an effect of suppressing adhesion of the contaminants M to the surface forming the second space 46B in the insulation member 41.

Additionally, similarly to the first structure example, the distance L3 between the discharging needle 73 (74) of the discharge electrode 70 and the sectioning portion 92 (upper end portion 92a) of the wall portion 90 is 30% or more and 68% or less (preferably 40% or more and 60% or less, or 50%) of the distance L1 between the discharging needle 73 (74) of the discharge electrode 70 and the opposed plate 61 (62) of the counter electrode 60. This suppresses discharging generated due to the discharging needle 73 (74) and the sectioning portion 92 provided close to each other, and effectively suppresses the contaminants M generated in the discharge region from passing through the gap between the discharging needle 73 (74) and the sectioning portion 92 and entering the side of the second space 46B.

Additionally, both of the distance between the discharging needle 73 and the sectioning portion 92 and the distance between the discharging needle 74 and the sectioning portion 92 may be 30% or more and 68% or less of the distance L1, but the present invention is not limited thereto. In other words, only the distance between the discharging needle 73 located on one side when viewed from the discharge electrode supporting portion 48 and the sectioning portion 92 may be within the above range, or only the distance between the discharging needle 74 located on the other side when viewed from the discharge electrode supporting portion 48 and the sectioning portion 92 may be within the above range.

The second structure example can be also used in combination with at least one of the first structure example described above and third and fourth structure examples to be described later. Additionally, when using the first structure example and the second structure example in combination, a ratio of the distance L2, L3 to the distance L1 may be within the range of 30% or more and 68% or less in both of the first and second structure examples, or the ratio of the distance L2, L3 to the distance L1 may be within the range in only one of the examples.

<Third Structure Example>

In the third structure example shown in FIG. 11, the wall portion 90 includes a plurality of projecting portions 93 provided on the surface of the insulation member 41. Accordingly, in the third structure example, provision of the plurality of projecting portions 93 enables an increase in the surface area of the surface of the insulation member 41. This enables a further increase in time until adhesion of the contaminants M to the surface of the insulation member 41 causes conduction between the discharge electrode 70 and the counter electrode 60. In other words, a creepage distance on the surface of the insulation member 41 can be increased.

In specific example of FIG. 11, the projecting portions 93 are provided on both the discharge electrode supporting portion 48 and the counter electrode supporting portion 44. The projecting portions 93 provided on the discharge electrode supporting portion 48 project to the side of the counter electrode supporting portion 44, and a gap is provided between distal end portions of the projecting portions 93 and the counter electrode supporting portion 44. Additionally, the projecting portions 93 provided on the counter electrode supporting portion 44 project to the side of the discharge electrode supporting portion 48, and a gap is provided between the distal end portions of the projecting portions 93 and the discharge electrode supporting portion 48. In FIG. 11, the projecting portions 93 provided on the discharge electrode supporting portion 48 and the projecting portions 93 provided on the counter electrode supporting portion 44, which are located opposed to each other with an interval, may be provided at positions displaced from each other.

The projecting portions 93 may be provided only on either one of the discharge electrode supporting portion 48 and the counter electrode supporting portion 44. Additionally, although the plurality of projecting portions 93 are provided in the specific example of FIG. 11, only one projecting portion 93 may be provided.

In the present embodiment, although the projecting portions 93 have a plate-shape which extends approximately in parallel to the discharge electrode supporting portion 48 over the entire region where the plurality of discharging needles 73 (74) are provided, the shape is not limited thereto. Each projecting portion 93 may have, for example, a shape projecting in a bar-form.

Additionally, in the third structure example, the projecting portions 93 also function as a barrier which suppresses the contaminants M from moving in the inner space of the recessed portion 46 (oval groove 46), i.e., the recessed inner space formed by the discharge electrode supporting portion 48 and the counter electrode supporting portion 44.

The third structure example can be also used in combination with at least one of the first and second structure examples described above and a fourth structure example to be described later.

<Fourth Structure Example>

In the fourth structure example shown in FIG. 12, the insulation member 41 has a plurality of hole portions 94 which pass through the insulation member 41. The hole portions 94 are provided in both the counter electrode supporting portion 44 and a bottom portion 95 of the supporting portion 47. Although an opening size of the hole portions 94 provided in the bottom portion 95 is larger than an opening size of the hole portions 94 provided in the counter electrode supporting portion 44, the size is not limited thereto.

In the fourth structure example, part of air containing the contaminants M and having reached close to the surface of the insulation member 41 flows out of the insulation member 41 through the hole portions 94. This enables reduction in an amount of adhesion of the contaminants M to the surface of the insulation member 41.

The fourth structure example shown in FIG. 12 is preferably used in combination with at least one of the first structure example, second structure example and third structure example described above. FIG. 12 illustrates a case where the extension portion 91 (the first structure example) indicated by a chain double-dashed line is used in combination with the fourth structure example.

[Air Cleaner]

Figure 13:
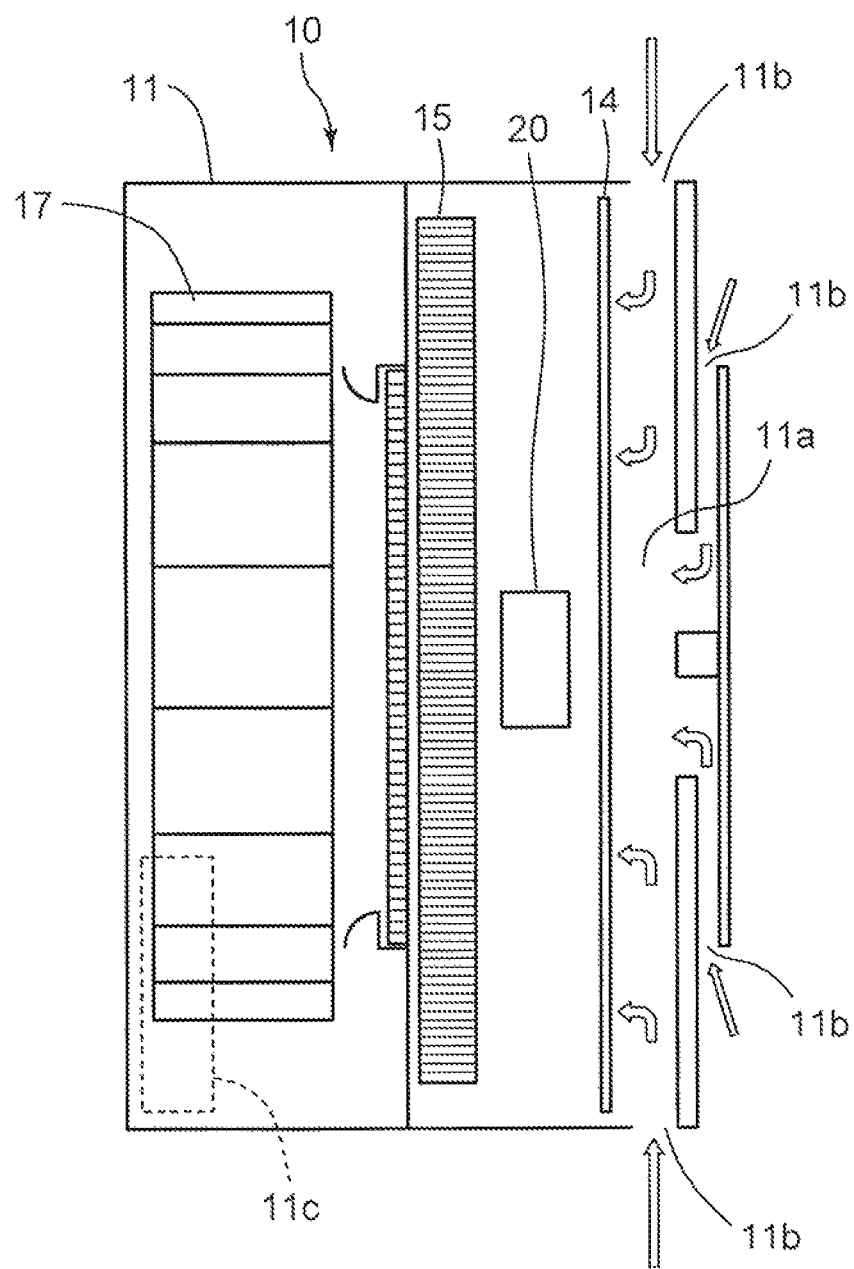
FIG. 13 is a schematic view showing another example of an air conditioning device including the discharge unit according to the embodiment of the present invention.

FIG. 13 is a schematic view showing another example of the air conditioning device 10 including the discharge unit 20 according to the embodiment of the present invention. The air conditioning device 10 shown in FIG. 13 is an air cleaner 10 for purifying air in a room space.

As shown in FIG. 13, the air cleaner 10 includes a box-shaped air-conditioning casing 11. Inside the air-conditioning casing 11, an air passage 11*a* is formed. The air-conditioning casing 11 has an air inlet port 11*b* communicating with the air passage 11*a*, and an air outlet port 11*c*. Air sucked from the air inlet port 11*b* into the air-conditioning casing 11 flows through the air passage 11*a* to be blown out of the air-conditioning casing 11 from the air outlet port 11*c*.

In the air passage 11*a*, a prefilter 14, a discharge unit 20, a catalyst filter 15, and a fan 17 are arranged sequentially from an upstream side (the air inlet port 11*b* side) of an air flow to a downstream side (the air outlet port 11*c* side).

The discharge unit 20 generates low-temperature plasma by streamer discharging, which is followed by generation of highly reactive activated species (high-speed electron, ion, radical, ozone, and the like) in the air. In the air cleaner 10 shown in FIG. 13, the same discharge unit 20 as those shown in FIG. 2 to FIG. 12 can be used. Additionally, also the prefilter 14, the catalyst filter 15, and the fan 17 are the same as the corresponding members of the above-described air conditioning device 10 shown in FIG. 1.

In the air cleaner 10, when the fan 17 is operated, air in the room space is sucked into the air passage 11*a* through the air inlet port 11*b*. This air passes through the prefilter 14. The prefilter 14 collects relatively large dusts in the air.

The air having passed through the prefilter 14 passes through the discharge unit 20. In the discharge unit 20, when a high voltage is supplied to the discharge electrode 70, streamer discharging progresses from the tip of each of the discharging needles 73 and 74 of the discharge electrode 70 toward the opposed plates 61 and 62 of the counter electrode 60 (see FIG. 6). When the discharging processing unit 40 generates a streamer discharge, activated species are resultantly generated in the air. As a result, harmful substances and odorous substances in the air are oxidized and decomposed by the activated species to purify the air.

The air having passed through the discharge unit 20 flows out of the discharge unit 20 together with the activated species to pass through the catalyst filter 15. The catalyst filter 15 adsorbs odorous substances and the like in the air. The adsorbed odorous substances are decomposed by the activated species to reproduce the adsorbent. Thus purified air is supplied to the room space through the air outlet port 11*c*.

The present invention is not limited to the above embodiment, but can be variously modified or improved without departing from the gist of the invention.

Although the embodiment in which the discharge unit 20 is mounted in the air conditioning device 10 has been illustrated, the discharge unit 20 can be also mounted in a device other than the air conditioning device 10.

Although the embodiment in which the discharge unit 20 is configured to have a streamer discharging system has been illustrated, discharging system is not limited to the streamer discharging, but may be other system of discharging.

The above embodiment will be outlined as follows.

The discharge unit of the present embodiment includes a discharge electrode, a counter electrode which is opposed to the discharge electrode, and an insulation member having a surface which is continuous from the discharge electrode to the counter electrode, in which a wall portion which is configured to suppress contaminants from adhering to the surface of the insulation member is provided on one side with respect to a discharge region formed by the discharge electrode.

In this configuration, provision of a wall portion on one side with respect to the discharge region formed by the discharge electrode suppresses conductive contaminants such as ammonium nitrate generated in the discharge region and tobacco stains contained in room air from adhering to the surface of the insulation member. This suppresses deterioration in insulating properties between the discharge electrode and the counter electrode in the insulation member having the surface continuous from the discharge electrode to the counter electrode.

In the discharge unit, a distance between the discharge electrode and the wall portion is preferably shorter than a distance between the discharge electrode and the counter electrode.

In this configuration, by setting the distance between the discharge electrode and the wall portion to be shorter than the distance between the discharge electrode and the counter electrode, the contaminants such as ammonium nitrate generated in the discharge region between the discharge electrode and the counter electrode and tobacco stains contained in room air are unlikely to pass through the gap between the discharge electrode and the wall portion. This further enhances an effect of suppressing adhesion of the contaminants to the surface of the insulation member.

In the discharge unit, the distance between the discharge electrode and the wall portion is preferably 30% or more and 68% or less of the distance between the discharge electrode and the counter electrode.

When the distance between the discharge electrode and the wall portion is less than 30% of the distance between the discharge electrode and the counter electrode, provision of the discharge electrode and the wall portion close to each other causes discharging to be generated easily. This makes it difficult to exhibit the original discharging performance between the discharge electrode and the counter electrode. By contrast, when the distance between the discharge electrode and the wall portion exceeds 68% of the distance between the discharge electrode and the counter electrode, contaminants easily pass through the gap between the discharge electrode and the wall portion, so that it is difficult to effectively suppress adhesion of the contaminants to the surface of the insulation member. Accordingly, the distance between the discharge electrode and the wall portion is preferably 30% or more and 68% or less of the distance between the discharge electrode and the counter electrode, more preferably 40% or more and 60% or less, and most preferably 50% in view of suppressing discharging between the discharge electrode and the wall portion, as well as effectively suppressing adhesion of the contaminants to the surface of the insulation member.

In the discharge unit, the wall portion may include an extension portion extending from a part, to which the counter electrode is attached, of the insulation member to a side of the discharge electrode.

In this configuration, the extension portion of the wall portion extends from the part to which the counter electrode is attached to the side of the discharge electrode, and thus effectively functions as a barrier which suppresses the contaminants generated in the discharge region between the discharge electrode and the counter electrode from entering the surface side of the insulation member.

In the discharge unit, the insulation member preferably has a recessed-shape.

In the above-described configuration, provision of the wall portion enables adhesion of the contaminants to the surface of the insulation member to be suppressed. However, it is difficult to completely prevent adhesion of the contaminants and it is inevitable that the contaminants are gradually adhered to the surface of the insulation member with a lapse of time of use. Thus, in this configuration, since a surface area of the insulation member is increased because the insulation member has a recessed-shape, time until adhesion of the contaminants to the surface of the insulation member causes conduction between the discharge electrode and the counter electrode can be further increased.

In the discharge unit, the insulation member may include a discharge electrode supporting portion which supports the discharge electrode, and a counter electrode supporting portion which supports the counter electrode, and the wall portion may include a sectioning portion which sections a recessed inner space formed with the discharge electrode supporting portion and the counter electrode supporting portion into a first space on a side of the discharge region and a second space on a side opposite to the discharge region with respect to the first space.

In this configuration, the sectioning portion of the wall portion sections a recessed inner space formed by the discharge electrode supporting portion and the counter electrode supporting portion into the first space on a side of the discharge region and the second space on the side opposite to the discharge region with respect to the first space. The second space is located at the side opposite to the discharge region with respect to the first space on the side of the discharge region. Accordingly, since the sectioning portion functions as a barrier, the contaminants are more unlikely to reach the second space as compared with the first space. Therefore, in this configuration, since it is possible to effectively suppress adhesion of the contaminants to the surface forming the second space out of the surface of the insulation member, deterioration in insulating properties between the discharge electrode and the counter electrode can be suppressed.

In the discharge unit, the wall portion may include one or a plurality of projecting portions provided on the surface of the insulation member.

In this configuration, provision of one or a plurality of projecting portions enables an increase in the surface area of the insulation member. As a result, time until adhesion of the contaminants to the surface of the insulation member causes conduction between the discharge electrode and the counter electrode can be further increased.

In this discharge unit, the insulation member may have one or a plurality of hole portions which passes through the insulation member.

In this configuration, since the insulation member is provided with one or a plurality of hole portions, part of air containing the contaminants and having reached close to the surface of the insulation member flows out of the insulation member through the hole portions. Accordingly, this enables reduction in an amount of adhesion of the contaminants to the surface of the insulation member.

What is claimed is:
1. A discharge unit comprising:
    a discharge electrode;
    a counter electrode opposed to the discharge electrode; and
    an insulation member having a surface, the surface being continuous from the discharge electrode to the counter electrode,
    a wall portion provided on one side with respect to a discharge region formed by the discharge electrode, the wall portion being configured to suppress a contaminant from adhering to the surface of the insulation member,
    the wall portion being at a position sandwiched by the discharge region and a space surrounded by the surface of the insulation member.
2. The discharge unit according to claim 1, wherein
    a distance between the discharge electrode and the wall portion is smaller than a distance between the discharge electrode and the counter electrode.

3. The discharge unit according to claim 2, wherein the distance between the discharge electrode and the wall portion is between 30% and 68% of the distance between the discharge electrode and the counter electrode.

4. The discharge unit according to claim 1, wherein the wall portion includes an extension portion extending from a part of the insulation member to which the counter electrode is attached to a side of the discharge electrode.

5. The discharge unit according to claim 1, wherein the insulation member has a recessed-shape.

6. The discharge unit according to claim 5, wherein the insulation member includes
a discharge electrode supporting portion supporting the discharge electrode and
a counter electrode supporting portion supporting the counter electrode, and
the wall portion includes a sectioning portion sectioning a recessed inner space formed with the discharge electrode supporting portion and the counter electrode supporting portion into
a first space on a side of the discharge region and
a second space on a side opposite to the discharge region with respect to the first space.

7. The discharge unit according to claim 1, wherein the wall portion includes at least one projecting portion provided on the surface of the insulation member.

8. The discharge unit according claim 1, wherein the insulation member has at least one hole portion passing through the insulation member.

9. The discharge unit according to claim 2, wherein the wall portion includes an extension portion extending from a part of the insulation member to which the counter electrode is attached to a side of the discharge electrode.

10. The discharge unit according to claim 2, wherein the insulation member has a recessed-shape.

11. The discharge unit according to claim 2, wherein the wall portion includes at least one projecting portion provided on the surface of the insulation member.

12. The discharge unit according to claim 2, wherein the insulation member has at least one hole portion passing through the insulation member.

13. The discharge unit according to claim 4, wherein the insulation member has a recessed-shape.

14. The discharge unit according to claim 4, wherein the wall portion includes at least one projecting portion provided on the surface of the insulation member.

15. The discharge unit according to claim 4, wherein the insulation member has at least one hole portion passing through the insulation member.

16. The discharge unit according to claim 5, wherein the wall portion includes at least one projecting portion provided on the surface of the insulation member.

17. The discharge unit according to claim 5, wherein the insulation member has at least one hole portion passing through the insulation member.

18. The discharge unit according to claim 7, wherein the insulation member has at least one hole portion passing through the insulation member.

* * * * *